United States Patent [19]

Haynes et al.

[11] 4,229,544
[45] Oct. 21, 1980

[54] LIVING ORGANISM PACKAGING

[75] Inventors: Robert W. Haynes; William H. Rasmussen, both of East Grand Forks, Minn.

[73] Assignee: Payfer Laboratories Inc., East Grand Forks, Minn.

[21] Appl. No.: 931,947

[22] Filed: Aug. 8, 1978

[51] Int. Cl.² ............... C12N 1/20; C12N 1/00
[52] U.S. Cl. ............... 435/253; 435/243; 435/254; 435/260; 435/299; 435/317; 435/810; 435/824; 435/831; 435/842; 435/874; 435/832; 435/878; 435/945; 435/853; 435/911; 71/7; 426/61; 426/410; 47/57.6; 206/213.1
[58] Field of Search ............... 195/54, 126; 426/61, 426/62, 410; 71/7; 435/243, 253, 254, 260, 299, 317, 810

[56] References Cited

U.S. PATENT DOCUMENTS

| | | | |
|---|---|---|---|
| 1,137,388 | 4/1915 | Earp-Thomas | 195/54 |
| 2,706,702 | 4/1955 | Carski | 195/126 |
| 3,098,016 | 7/1963 | Cooper | 195/102 |
| 3,228,838 | 1/1966 | Rinfert | 34/5 |
| 3,705,813 | 12/1972 | Vogel et al. | 426/410 |
| 3,860,490 | 1/1975 | Guttag | 195/108 |
| 3,893,892 | 7/1975 | Mehl | 195/127 |

*Primary Examiner*—Lionel M. Shapiro
*Attorney, Agent, or Firm*—Cushman, Darby & Cushman

[57] ABSTRACT

A method of packaging, and the package so produced, for maintaining living organisms viable for a long period of time. The living organisms, such as bacteria, fungi, algae, etc., are mixed with a carrier, such as peat. The organism-carrier mixture is then disposed in a package, such as a heat-sealable plastic envelope, and a gaseous atmosphere is provided in the package effective to induce and maintain substantial nonvegatative state formation of the organisms. Some organisms will form cysts, others spores, but whatever nonvegetative state is assumed, the organisms will be much less susceptible to heat, cold, starvation, and other adverse environmental factors. Suitable gaseous atmospheres include nitrogen, helium, and argon gases. The package is then sealed to prevent contamination of the atmosphere therein.

24 Claims, 2 Drawing Figures

LIVING ORGANISM PACKAGING

BACKGROUND AND SUMMARY OF THE INVENTION

The invention relates to a method of packaging living organisms so that they can be stored for a long period of time in adverse environmental conditions yet while still remaining viable, and to a package produced thereby. Conventionally, it is difficult, if not impossible, to package living organisms, such as nitrogen fixing bacteria and the like, so that they can be handled normally, shipped, and stored, without resulting in death of the organisms. Microorganisms are extremely vulnerable to death from starvation, heat, cold, airborne chemicals, and other environmental factors, and packaging them in conventional containers substantially reduces the number of viable organisms that can be delivered for a given end use.

Containers to adequately protect microorganisms in their vegetative state normally are too expensive to achieve widespread use, are generally nondisposable, and often require special handling—yet still are effective only for relatively short periods of time. Also, sterile conditions often are required during packaging, or other special conditions.

According to the present invention, a packaging method, and the package so produced, are provided that essentially overcome all of the above-mentioned problems with respect to microorganism packaging. According to the present invention, a large number of viable microorganisms can be delivered in a form eminently suited for a desired end use in an inexpensive and simple manner. According to the present invention, no special handling is necessary, although a large number of viable microorganisms can still be delivered even after long storage periods.

According to the present invention, the microorganisms are induced to assume a nonvegetative state in which the organisms are dormant. In such a state, whether it be a cyst or spore, the microorganisms are much better able to resist temperature changes and chemicals, and because they are dormant, do not require food. Also, since competing organisms will also become dormant, there is no need to ensure sterility of the microorganism carrier.

According to the method of the present invention, packaging of living organisms is practiced consisting essentially of the steps of mixing the living organisms with a carrier; disposing the organism-carrier mixture in a package; providing a gaseous atmosphere in the package effective to induce and maintain substantial nonvegetative state formation of the organisms; and sealing the package to prevent contamination of the atmosphere therein. The atmosphere providing step may be accomplished by providing an atmosphere selected from the group consisting essentially of nitrogen, helium and argon gases, although other gases may be effective to induce and maintain substantial nonvegetative state formation depending upon the particular microorganism. Peat has been found to be an effective carrier, although other carriers may also be effective depending upon the particular organism and the end use to which it should be put. In particular, the carrier may comprise a substantially granular material suitable for maintaining the organisms in a viable condition over a long period of time and for effecting utilization of the organisms for end purposes.

The invention is not limited to the particular type of microorganism packaged, and any microorganism capable of nonvegetative state formation as a result of exposure to a given gaseous atmosphere is considered within the scope of the invention. However, the invention is especially suitable for agricultural uses. For instance, with the decreasing availability of natural gas and petroleum products, other sources of agricultural nitrogen supplements are becoming feasible. For instance, nitrogen fixing bacteria, such as Azotobacter chroococcum, have been found effective in greatly increasing nitrogen levels when applied to plant roots, seeds, or the like. Packaging of the microorganisms with a carrier, such as peat, which facilitates the application of the microorganisms over a large volume of seed, roots, or the like, while providing an environment in which the microorganisms can live, can be extremely effective in providing marketability of such microorganisms.

Similarly, according to the present invention, a package of living organisms is provided consisting essentially of the living organisms mixed with a carrier; gaseous atmosphere means for inducing and maintaining substantial nonvegetative state formation with the organisms; and a sealed envelope surrounding the carrier, organisms, and atmosphere for preventing contamination of the atmosphere. The sealed envelope may be opaque, or an opaque label may be employed.

It is the primary object of the present invention to provide a method of packaging, and a resultant package, which preserves microorganism viability in an inexpensive manner even over long periods of time despite adverse environmental conditions. This and other objects of the invention will become clear from an inspection of the detailed description of the invention, and from the appended claims.

DETAILED DESCRIPTION OF THE INVENTION

Figure 1:
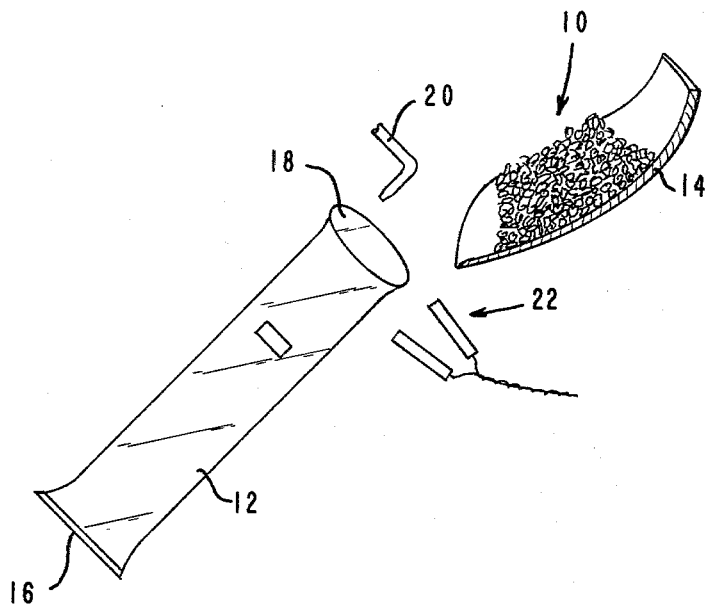
FIG. 1 is a schematic perspective view of a package according to the invention during the packaging operation.

The invention relates to a method of packaging living organisms, and the package so produced. An exemplary manner of packaging living organisms according to the present invention may be understood with specific reference to FIG. 1, although it is to be understood that such manner is nonlimiting.

Living organisms, such as bacteria, algae, fungi, protozoa, etc. are mixed with a carrier to provide an organism-carrier mixture, as shown schematically at 10 in the drawings. A package, shown generally at 12 in the drawings, is provided for receipt of the organism-carrier mixture, and a gaseous atmosphere is provided in the package. The gaseous atmosphere is effective to induce and maintain substantial nonvegetative state formation of the organisms. The package is then sealed to prevent contamination of the atmosphere therein.

In the embodiment illustrated in FIG. 1, the microorganism-carrier mixture 10 is provided on a scoop 14, or other suitable implement, which facilitates the disposition of the mixture 10 into a flexible plastic pouch 12 sealed at one end 16 thereof, and open at the other end 18 thereof. A suitable inert gas atmosphere is then introduced into the pouch 12 and it is sealed. The introduction of the inert atmosphere and subsequent sealing can be practiced utilizing a suitable conventional machine, such as a Herfurth Typ. WIG 107. Such machines include a gas introduction nozzle, shown schematically at 20 in FIG. 1, and heat sealing components, shown schematically at 22 in FIG. 1, for sealing the open end 18. The inert gases introduced, sealing of the open end 18 is effected, and the package that results is shown generally at 24 in FIG. 2.

Figure 2:
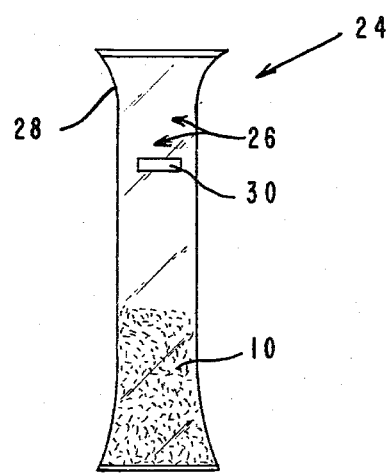
FIG. 2 is a frontal view of an exemplary completed package according to the invention.

The package 24 illustrated in FIG. 2 is an exemplary package according to the present invention, and includes the living organism-carrier mixture 10, gaseous atmosphere means indicated at 26, for inducing and maintaining substantial nonvegetative state formation of the organisms, and a sealed, gas-tight envelope 28 surrounding the carrier, organisms, and atmosphere for preventing contamination of the atmosphere 26. A suitable label 30 may be provided on the envelope 28 for indicating the contents and/or use of the organism-carrier mixture 10, and the envelope 28 may be transparent or under some circumstances opaque, for an opaque label may be provided substantially covering the entire package 28.

It is to be understood that the present invention is not limited to the particular microorganisms packaged, but in general any living organism capable of easy packaging and long shelf life is within the scope of the invention. In particular, any organism capable of substantial nonvegetative state formation upon exposure of that organism to a particular gaseous atmosphere is within the scope of the invention. Some organisms, such as genus Azotobacter bacteria, will form cysts upon exposure to particular inert gaseous atmospheres (i.e. nitrogen), whereas other organisms, such as certain fungi and certain bacteria, will form spores. The particular nonvegetative form that the organism assumes is not limiting of the scope of the invention.

Exemplary organisms that may be packaged according to the present invention include organisms from the genera Azotobacter, Achromobacter, Beijerinckia, Clostridium, Pseudomonas, Bacillus, Rhizobium, Trichoderma, Anabaena, Cylindrospermum, Nostoc, Volvox, Oscillaria, and Lactobacillus. A wide variety of root zone microorganisms, fermentation microorganisms, and mamamalian gut and rumen microorganisms are packagable. Specific species that are packagable according to the present invention are: *Azotobacter vinelandii, Azotobacter agile, Azotobacter chroococcum* (strains adapted for wheat, sugar beet, sunflower, potato, corn, soybean, pinto bean, sorghum, oats, barley, flax, rape and garden crops), *Rhizobium leguminosarum, Rhizobium phaseoli, Rhizobium trifoli, Rhizobium meliloti, Rhizobium lupini, Rhizobium juponicum, Bacillus megaterium, Pseudomonas radiobacter, Achromobacter geminum, Lactobacterium plantarum, Clostridium pasteurianum, Trichoderma harzianum, Trichoderma lignorum, Oscillaria rubescens,* and *Volvox aureus.*

The invention also is not limited to a specific carrier since the carrier will depend upon the particular microorganism and gaseous atmosphere employed. However, one carrier that has been found to be eminently suited for packaging microorganisms according to the present invention is peat—especially peat with a pH controlling substance therein, such as calcium carbonate. Another suitable carrier is whey. In general, the carrier comprises a substantially granular material suitable for maintaining the organisms in a viable condition over a long period of time and for effecting application of the organisms in the carrier to plant roots, seeds, or the like. Such granular carriers are especially suited for spreading the microorganisms over a large volume of seeds when the microorganisms are used as a seed innoculent, and for applying them to plant roots when the microorganisms are used as a soil treatment, or the like. Other carriers could be employed depending upon the end use, such as a carrier suitable for use as a foliar spray.

The invention is not limited to a particular gaseous atmosphere, but rather any inert gas, or combination of gases, that achieve the desired results according to the present invention of maintaining substantial microorganism viability over long periods of time despite adverse environmental conditions, is suitable. Gaseous atmospheres effective to induce and maintain substantial nonvegetative state formation of the organisms are within the scope of the present invention, and include nitrogen, helium, and argon gases.

The following examples will further illustrate the invention:

EXAMPLE 1

Azotobacter chroococcum (wheat strain) microorganisms were prepared in a growth medium that included $CaCl_2$—0.2 g.; $MgSO_4.7H_2O$—0.24 g.; $K_2HPO_4$—3.02 g.; $NaH_2PO_4$—9.5 g.; Fe Citrate—0.01 g.; traces of Mn, Cu, Zn, B, and Mo; 2 liters $H_2O$; Agar—24 g; Mannitol—20 g. The microorganisms on growth media were packaged with approximately $10^7$ Azotobacter chroococcum per gram of peat carrier. One sample of bacteria and carrier was disposed in a commercial sealed package (Soeco bag) while another sample was disposed in a sealed gas-tight plastic envelope with a nitrogen atmosphere. After three months, the packages were opened and the viability of the bacteria therein was determined. The nitrogen gas packaged bacteria sample had 1.83 times the number of active viable bacteria as the commercially sealed package.

EXAMPLE 2

Azotobacter chroococcum (potato strain) microorganisms were prepared on a growth medium as in Example 1, and mixed with a peat carrier, in the proportion of $10^6$ Azotobacter per gram of peat. One series of samples of the bacteria-carrier mixture was provided in plastic Soeco bags, as is conventional, while another set of samples were provided in sealed gas-tight plastic bags containing a nitrogen atmosphere. After about five months, the bags were opened and it was found that the nitrogen gas packed bags had multiples of $10^5$ Azotobacter chroococcum per gram of peat, while the Soeco bags had multiples of $10^3$ viable Azotobacter chroococcum per gram of peat.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent methods and packages.

What is claimed is:

1. A method of packaging living organisms consisting essentially of the steps of
    mixing the living organisms with a carrier comprising substantially granular material suitable for maintaining the organisms in a viable condition over a long period of time, disposing the organism-carrier mixture in a package, providing a gaseous atmosphere in the package effective to induce and maintain substantial nonvegetative state formation of the organisms, and sealing the package to prevent contamination of the atmosphere therein until breakage of the seal just before use of the organisms.

2. A method as recited in claim 1 whereiN the package comprises heat-sealable flexible sheet material, and wherein said sealing step is practiced by heat-sealing the package.

3. A method as recited in claim 1 wherein said atmosphere providing step is accomplished by providing an atmosphere selected from the group consisting essentially of nitrogen, helium, and argon gases.

4. A method as recited in claim 1 wherein the living organisms are selected from the group consisting of the genera Azotobacter, Achromobacter, Beijerinckia, Clostridium, Pseudomonas, Bacillus, Rhizobium, Trichoderma, Anabaena, Cylindrospermum, Nostoc, Volvox, Oscillaria, and Lactobacillus.

5. A method as recited in claim 4 wherein the living organisms selected from the genus Azotobacter are selected from the group consisting of the species *vinelandii, agile,* and *chroococcum.*

6. A method as recited in claim 4 wherein the living organisms selected from the genus Rhizobium are selected from the group consisting of the species *leguminosarum, phaseoli, trifoli, meliloti, lupini,* and *juponicum.*

7. A method as recited in claim 1 wherein the carrier is selected from the group consisting essentially of peat and whey.

8. A method as recited in claim 1 comprising the further steps of breaking the seal of and opening the package after an extended storage period, and applying the organisms with the carrier to plant roots or seeds.

9. A package of living organisms consisting essentially of living organisms mixed with a carrier comprising a substantially granular material suitable for maintaining the organisms in a viable condition over a long period of time, gaseous atmosphere means for inducing and maintaining substantial nonvegetative state formation of the organisms, and a sealed envelope surrounding said carrier, organisms, and atmosphere for preventing contamination of said atmosphere until breakage of the envelope seal just before use of the organism.

10. A package as recited in claim 9 wherein said atmosphere means comprises a gas selected from the group consisting essentially of nitrogen, helium and argon gases.

11. A package as recited in claim 9 wherein said envelope comprises a member formed of flexible sheet material.

12. A package as recited in claim 9 or claim 11 wherein said envelope is opaque.

13. A package as recited in claim 11 wherein said envelope flexible sheet material is formed of heat-sealable material.

14. A package as recited in claim 9 wherein the living organisms are selected from the group consisting of the genera Azotobacter, Achromobacter, Beijerinckia, Clostridium, Pseudomonas, Bacillus, Rhizobium, Trichoderma, Anabaena, Cylindrospermum, Nostoc, Volvox, Oscillaria, and Lactobacillus.

15. A package as recited in claim 14 wherein the living organisms selected from the genus Azotobacter are selected from the group consisting of the species *vinelandii, agile,* and *chroococcum.*

16. A package as recited in claim 14 wherein the living organisms selected from the genus Rhizobium are selected from the group consisting of the species *leguminosarum, phaseoli, trifoli, meliloti, lupini,* and *juponicum.*

17. A package as recited in claim 9 wherein said carrier is selected from the group consisting essentially of peat, and whey.

18. A package as recited in claim 9 wherein said carrier comprises peat with a pH controlling substance.

19. A package as recited in claim 20 wherein the pH controlling substance is calcium carbonate.

20. A package of living organisms of the genus Azotobacter, a carrier for the organisms comprising a substantially granular material suitable for maintaining the organisms in a viable condition over a long period of time and effecting utilization of the organisms for application to plants, seed, and the like, an inert gas atmosphere in the package effective to induce and maintain substantial nonvegetative state formation, and a gas-tight envelope containing the organism-carrier mixture and atmosphere.

21. A package as recited in claim 22 wherein the carrier is peat and the gas is nitrogen.

22. A method as recited in claim 1 wherein the carrier is peat and comprising the further step of providing a pH controlling substance with the peat.

23. A method as recited in claim 22 wherein the pH controlling substance is calcium carbonate.

24. A package as recited in claim 9 wherein said carrier further comprises a material suitable for effecting application of the organisms in the carrier to plant roots, seeds, and the like.

* * * * *